(12) United States Patent
Goodman et al.

(10) Patent No.: US 6,348,203 B1
(45) Date of Patent: Feb. 19, 2002

(54) NITROIMIDAZOLE GEL COMPOSITION

(75) Inventors: Michael Goodman, Ampthill (GB); Ake Lindahl, Skurup (SE)

(73) Assignee: Biogland Ireland (R&D) Limited, Dublin (IE)

( * ) Notice: Subject to any disclaimer, the term of this patent is extended or adjusted under 35 U.S.C. 154(b) by 0 days.

(21) Appl. No.: 09/331,367

(22) PCT Filed: Dec. 19, 1997

(86) PCT No.: PCT/GB97/03512

§ 371 Date: Jun. 16, 2000

§ 102(e) Date: Jun. 16, 2000

(87) PCT Pub. No.: WO98/27960

PCT Pub. Date: Jul. 2, 1998

(30) Foreign Application Priority Data

Dec. 20, 1996 (GB) .................................................. 9626513

(51) Int. Cl.⁷ .................................................. A61K 7/00
(52) U.S. Cl. ........................................ 424/401; 514/861
(58) Field of Search ............................ 424/401; 514/861

(56) References Cited

U.S. PATENT DOCUMENTS 5,536,743 A * 7/1996 Borgman .................... 514/39.8
5,662,924 A * 9/1997 Rhodes ........................ 424/445

FOREIGN PATENT DOCUMENTS

| GB | 2229443 | * | 9/1990 |
| WO | 9320817 | * | 10/1993 |

* cited by examiner

*Primary Examiner*—Jose G. Dees
*Assistant Examiner*—Michael A. Williamson
(74) *Attorney, Agent, or Firm*—Ropes & Gray

(57) ABSTRACT

A viscous hydrogel composition, for use in a topical treatment of a skin condition involving dry or inflamed skin, comprising an antimicrobially active nitroimidazole drug, a water miscible alkylene glycol, a bydroxyalkyl cellulose gelling agent and water, buffered to have a physiologically acceptable pH and a method of making the same.

44 Claims, No Drawings

NITROIMIDAZOLE GEL COMPOSITION

BACKGROUND OF THE INVENTION

The present invention relates to viscous, jelly or cream like, pharmaceutical compositions for skin application, preferably for use in topical treatments of skin which is intolerant of exposure to aqueous preparations of non-physiological pH, or of excessive hypo- or hypertonicity. The invention also relates to a method of preparing such compositions.

Antimicrobially active imidazole derivatives, such as the nitroimidazole compounds metronidazole and tinidizole, can be used in the topical treatment of certain dermatological diseases, including rosacea and eczema, in which the skin becomes dry or inflamed, or is predisposed to becoming dry or inflamed when exposed to aqueous media. Dry or inflamed skin is highly intolerant of exposure to water based formulations with a pH outside the physiologically acceptable range of approximately pH 5–6, or which exert a physiologically incompatible osmotic pressure. Thus, topically applied aqueous compositions with an inappropriately high or low pH, or which exert an incompatible osmotic pressure, not only have the potential to cause irritation and stinging, but their use can actually worsen the symptoms of a disease.

With some active agents, this problem can be overcome by employing oil based formulations. However, many antimicrobially active imidazole derivatives are substantially insoluble in such non-polar vehicles and, therefore, cannot be formulated in this manner.

One known aqueous based metronidazole gel composition includes lactic acid both as an humectant and in order to increase the solubility of the metronidazole. However, the presence of lactic acid in this formulation causes it to have a low pH and to be prone to causing an unacceptable degree of irritation to dry, sensitive or disease inflamed skin.

Other known topical metronidazole formulations include cross-linked polymers of acrylic acid, sold under the registered trade mark CARBOPOL, as thickening agents. Although it is possible to use such thickeners to prepare gels with a pH in the range of 5–6, unless great care is exercised during the manufacture of formulations employing these materials, they can form clumps which are insoluble, due to the formation of a water impregnable layer around the clump interior, and which cannot be reduced or dissolved once formed. In such circumstances, hydration of the resin will be incomplete and the result can be broad pH fluctuations in the final product. Moreover, polyacrylic acid resins are sensitive to salts and cations and are not stable in the presence of more than about 0.1% of strongly ionizable salts, particularly those with multivalent cations, such as calcium, magnesium, iron and aluminum salts. Thus, not only is it difficult to manufacture such formulations consistently within an acceptable (narrow) pH range, but it may also be impossible to include therein a sufficient amount of ionic material to achieve an ideal pH, mitigate clumping induced pH variation, or to achieve a skin compatible osmotic pressure.

An object of the present invention is to provide a viscous composition useful in the topical treatment of highly sensitive skin with water soluble active agents, such as metronidazole, which is less prone to irritate inflamed or sensitive skin and which is more easily and more readily manufactured than known such products.

SUMMARY OF THE INVENTION

In a first aspect, the present invention provides a method for preparing a viscous hydrogel composition, for use in a topical treatment of a skin condition involving dry or inflamed skin, including a pharmaceutically active agent, a polysaccharide, a water-miscible organic solvent and water, comprising the steps of suspending the polysaccharide in the water-miscible organic solvent and mixing the resulting polysaccharide suspension into the aqueous medium, thereby to hydrate the polysaccharide and to form a viscous hydrogel composition, wherein the pharmaceutically active agent is an antimicrobially active nitroimidazole drug, the water-miscible organic solvent is a water-miscible alkylene glycol, and the composition is buffered to have a pH within the range of 4.5–6.5. The polysaccharide, preferably acts as a gelling or thickening agent. An advantage of this aspect of the invention is that it enables clumping of the polysaccharide, and consequential broad pH fluctuations in the final product, to be avoided and thereby allows the aforementioned object of the invention to be achieved.

Preferably, the aqueous medium comprises a previously formed aqueous solution of the nitroimidazole drug. Alternatively or additionally, the active agent can be mixed with the water-miscible organic solvent before the suspension is mixed with the aqueous medium. In this alternative procedure, the active agent can be suspended or dissolved in the water-miscible organic solvent and is preferably mixed therewith before the polysaccharide is suspended therein.

The active agent can be dissolved in water at a temperature of 15–50° C., 25–40°C. and, preferably, 35–40° C. (to provide the aqueous medium) and the suspension of polysaccharide can be at a temperature of 4–30° C., preferably 15–25° C., or 4–15° C., preferably 10–15° C., immediately prior to mixing with the aqueous medium. It is preferred for the polysaccharide to be insoluble or substantially insoluble in the organic solvent.

In an embodiment of the first aspect of the invention, the polysaccharide is preferably a non-ionic cellulose ester, ether, hydroxy-ether, or hydroxy-ester, or a non-ionic starch derivative. The polysaccharide can be a methyl, ethyl or propyl cellulose ester, ether, hydroxy-ether or hydroxy-ester. Preferably, the polysaccharide is a hydroxyalkyl cellulose.

In accordance with a second aspect of the present invention there is provided a viscous hydrogel composition, for use in a topical treatment of a skin condition involving dry or inflamed skin, comprising an antimicrobially active nitroimidazole drug, a water miscible alkylene glycol, a hydroxyalkyl cellulose gelling agent and water, buffered to have a pH within the range of 4.5–6.5 and having a viscosity within the range of 10 Pa·s (10,000 cps) and preferably 50 to 200 Pa·s (50,000 to 200,000 cps).

Since they can be manufactured using processes, such as those according to the first aspect of the invention, which allow clumping to be avoided, an advantage of compositions in accordance with this aspect of the invention is that they can be produced consistently and within an acceptably narrow pH range.

In a third aspect, the invention provides a viscous hydrogel composition, for use in a topical treatment of a skin condition involving dry or inflamed skin, prepared or preparable by a method in accordance with the first aspect of the invention, and having a viscosity within the range of 10 Pa·s (10,000 cps) and preferably 50 to 200 Pa·s (50,000 to 200,000 cps).

Unlike previous compositions, compositions in accordance with the second aspect of the invention are, and those prepared in accordance with the first aspect can be, buffered, for example by the inclusion therein of ionic buffers such as conventional weak acid/salt buffers. By so doing, it is easy to ensure that such compositions will have a pH within a physiologically acceptable pH range, and that any tendency they otherwise could have to clumping induced pH variation, or pH drift during storage and after application to the skin, is mitigated or reduced below an acceptable limit.

Accordingly, in embodiments of all the aspects of the invention, suitable buffering agents are selected so that the pH of and, in some embodiments, the osmotic pressure exerted by the composition is physiologically acceptable, not only immediately on application to the skin but, preferably, also for a sufficient period thereafter to prevent irritation through pH (or osmotic pressure) drift after application to the skin.

Suitable buffers include acetic acid/acetate, hydrochloric acid/citrate, citro-phosphate, phosphate, phosphate buffered saline, and citric acid/citrate systems. The preferred buffering agents are citric acid and a citrate, preferably sodium citrate, and, in preferred embodiments, the inventive composition has a pH within the range of 4.5–6.5, preferably within the range of 5–6 and, more preferably, of about 5.5. In preferred embodiments of the first aspect of the invention, buffering agents are included in the aqueous medium before the suspended polysaccharide thickening agent is mixed with said solution.

Preferably, the method in accordance with the first aspect of the invention is employed to prepare a composition in accordance with the second aspect of the invention.

The hydroxyalkyl cellulose gelling agent can be hydroxymethyl, hydroxyethyl or hydroxypropyl cellulose. The preferred such agent is hydroxyethyl cellulose.

It is preferred that the hydroxyalkyl cellulose gelling agent is insoluble or substantially insoluble in the water miscible alkylene glycol (when substantially pure). Suitable alkylene glycols include glycerol, dipropylene glycol, polyethylene glycol, propylene carbonate, propylene glycol, butylene glycol, pentylene glycol and hexylene glycol. The preferred alkylene glycol is propylene glycol.

It is preferred that the nitroimidazole drug is the sole pharmaceutically active agent used in methods and compositions in accordance with the invention. Metronidazole or tinidazole are the preferred nitroimidazole drugs, the most preferred being metronidazole.

Preferred embodiments of the invention have a viscosity within the range of 10 Pa·s (10,000 cps) and preferably 50 to 200 Pa·s (50,000 to 200,000 cps).

Preferably, compositions in accordance with or prepared by the invention are for use in treating skin conditions involving dry or inflamed skin, including rosacea, eczema and conditions involving infections responsive to anti-microbially active imidazole derivatives such as metronidazole. The latter include those conditions which are caused or exacerbated by organisms responsive to anti-microbially active imidazole derivatives, including infected fungating tumors and benign cutaneous ulcers.

It is preferred that compositions in accordance with or prepared by the invention exert a physiologically acceptable osmotic pressure.

In a further aspect, the invention provides the use of a composition in accordance with the second or third aspect of the invention or a composition prepared by a method in accordance with the first aspect of the invention, for the preparation of a medicament for use in treating a skin condition involving dry or inflamed skin, including rosacea, eczema and conditions involving infections responsive to anti-microbially active nitroimidazole derivatives, preferably metronidazole (the latter including those conditions which are caused or exacerbated by organisms responsive to anti-microbially active imidazole derivatives). In another aspect, the invention comprises the use of a nitroimidazole drug for the preparation of a medicament in accordance with the second or third aspect of the invention, for use in treating a skin condition involving dry or inflamed skin, preferably one of the aforementioned conditions.

In a yet further aspect, the invention provides a method of treating a skin condition involving dry or inflamed skin, preferably rosacea, eczema or a condition involving an infection responsive to an antimicrobially active nitroimidazole drug, preferably metronidazole, comprising topically applying a composition in accordance with the second or third aspect of this invention to skin effected by said condition.

DETAILED DESCRIPTION OF THE INVENTION

Preferred, non-limiting examples of the invention, in its various aspects, will now be described.

EXAMPLE 1

The materials employed in this example are set out in the following table.

| | | |
|---|---|---|
| Metronidazole | 0.75% | |
| Water | to 100% | |
| Citric acid | Q.S. | } To provide pH 5.5 |
| Sodium Citrate | Q.S. | |
| Hydroxyethyl Cellulose | 1.8% | |
| Propylene Glycol | 5.0% | |
| Methyl-p-benzoic acid ester | 0.15% | |
| Propyl-p-benzoic acid ester | 0.05% | |

In a first vessel, the metronidazole is dissolved in the water at a temperature of 35–40° C. and sufficient quantities of the buffering agents, citric acid and sodium citrate, are then added to the resulting solution, to provide the finished composition with a pH of 5.5. Conventional preservatives (not listed above) may also be included in the solution.

In a separate vessel, the preservatives methyl-p-benzoic acid ester and propyl-p-benzoic acid ester are dissolved in the propylene glycol and the hydroxyethyl cellulose is added to the resulting solution, to form a suspension. This suspension is then cooled to 10–15° C. and then added to the first vessel, containing the buffered aqueous metronidazole solution, while the latter is vigorously stirred. Stirring is continued until the hydroxyethyl cellulose is fully hydrated. After the resulting mixture has become homogeneous, it is allowed to stand for one day and the resulting gel is then packed.

EXAMPLE 2

The same materials are employed in this example in the same quantities as are employed in Example 1 above. Sufficient quantities of citric acid and sodium citrate are dissolved in the required amount of water to provide the finished composition with a pH of 5.5. Conventional preservations (not listed) can be included in this solution. In a separate vessel, the methyl-p-benzoic acid ester and the propyl-p-benzoic acid ester are dissolved in the propylene glycol, and the metronidazole followed by the hydroxyethyl cellulose are added to the resulting solution, to form a suspension. This suspension is then cooled to 10–15° C. and added to a second vessel containing the citrate buffered aqueous solution, while the latter is vigorously stirred. Stirring is continued until the hydroxyethyl cellulose is fully hydrated. After the resulting mixture has become homogeneous, it is allowed to stand for one day and the resulting gel is then packed.

EXAMPLE 3–12

Further compositions are made up using the materials and methods described in Examples 1 and 2,but with the citric acid and sodium citrate being replaced with acetic acid and sodium acetate (examples 3 and 4), hydrochloric acid and sodium citrate (examples 5 and 6), disodium hydrogen orthophosphate and citric acid (examples 7and 8), disodium hydrogen orthophosphate and potassium dihydrogen orthophosphate (examples 9 and 10), and disodium hydrogen orthophosphate, potassium dihydrogen orthophosphate and sodium chloride (examples 11 and 12), respectively.

EXAMPLE 13

Twelve patients suffering from rosacea with mild to severe erythema and a minimum of three pustules or papules on the face were treated with a 0.75% metronidazole gel over a period of nine weeks. The metronidazole gel was topically applied on a twice daily basis. By week nine, the papule/pustule count was reduced by 50% or more in all patients, with 100% clearing in 75% of the patients. The degree of erythema exhibited by all of the patients in the group improved significantly, from being relatively severe at the outset to being relatively mild at the end of the nine week period of the test.

What is claimed is:

1. A method of preparing a viscous hydrogel composition, for use in a topical treatment of a skin condition involving dry or inflamed skin, including a pharmaceutically active agent, a polysaccharide, a water-miscible organic solvent and water, comprising the steps of suspending the polysaccharide in the water-miscible organic solvent and mixing the resulting polysaccharide suspension into an aqueous medium, wherein the pharmaceutically active agent is present in the aqueous medium, the suspension, or both, thereby to hydrate the polysaccharide and to form a viscous hydrogel composition, wherein the pharmaceutically active agent is an antimicrobially active nitroimidazol drug, the water-miscible organic solvent is a water-miscible alkylene glycol, and the composition is buffered with an ionic buffer to have a pH within the range of 4.5–6.5.

2. A method as claimed in claim 1, wherein the nitroimidazole drug is dissolved in the aqueous medium, or suspended or dissolved in the water miscible organic solvent, before said suspension is mixed with said aqueous medium.

3. A method as claimed in claim 2, wherein the nitroimidazole drug is suspended or dissolved in the water-miscible organic solvent, before the polysaccharide is suspended therein.

4. A method as claimed in claim 2, wherein the nitroimidazole drug is dissolved in the aqueous medium at a temperature in the range of 15–50° C.

5. A method as claimed in claim 2, wherein the nitroimidazole drug is dissolved in the aqueous medium at a temperature in the range of 25–40° C.

6. A method as claimed in claim 2, wherein the nitroimidazole drug is dissolved in the aqueous medium at a temperature in the range of 35–40° C.

7. A method as claimed in claim 1, wherein the polysaccharide suspension is at a temperature in the range of 4–30° C. immediately prior to mixing with the aqueous medium.

8. A method as claimed in claim 1, wherein the polysaccharide suspension is at a temperature in the range of 4–15° C. immediately prior to mixing with the aqueous medium.

9. A method as claimed in claim 1, wherein the nitroimidazole drug is metronidazole or tinidazole.

10. A method as claimed in claim 9, wherein the nitroimidazole drug is metronidazole.

11. A method as claimed in claim 1, wherein the buffer is included in the aqueous medium before the suspended polysaccharide is mixed with said medium.

12. A method as claimed in claim 1, wherein the buffer comprises a buffer comprises a buffer system selected from the group consisting of acetic acid/acetate, citric acid/citrate, citro-phosphate, phosphate and phosphate buffered saline.

13. A method as claimed in claim 12, wherein the buffer system comprises citric acid and a citrate.

14. A method as claimed in claim 1, wherein the composition has a pH within the range of 5–6.

15. A method as claimed in claim 14, wherein the composition has a pH of about 5.5.

16. A method as claimed in claim 1, wherein the polysaccharide is selected from the group consisting of non-ionic cellulose esthers, non-ionic cellulose hydroxy-ethers, non-ionic cellulose hydroxy-esters, and non-ionic starch derivatives.

17. A method as claimed in claim 16, wherein the polysaccharide is selected from the group consisting of methyl, ethyl and propyl cellulose esthers, hydroxy-ethers and hydroxy-esters.

18. A method as claimed in claim 1, wherein the polysaccharide is a hydroxyalkyl cellulose.

19. A method as claimed in claim 18, wherein the hydroxyalkyl cellulose is hydroxymethyl, hydroxyethyl or hydroxypropyl cellulose.

20. A method as claimed in claim 19, wherein the hydroxyalkyl cellulose is hydroxyethyl cellulose.

21. A method as claimed in claim 1, wherein the polysaccharide is insoluble or substantially insoluble in the water miscible organic solvent.

22. A method as claimed in claim 1, wherein the water-miscible alkylene glycol is selected from the group consisting of glycerol, dipropylene glycol, propylene glycol, butylene glycol, pentylene glycol and hexylene glycol.

23. A method as claimed in claim 22, wherein the water miscible alkylene glycol is propylene glycol.

24. A viscous hydrogel composition for use in a topical treatment of a skin condition involving dry or inflamed skin, comprising an antimicrobially active nitroimidazol drug, a water-miscible alkylene glycol, a polysaccharide, water and an ionic buffer, said composition being buffered to have a pH within the range of 4.5–6.5.

25. A viscous hydrogel composition as claimed in claim 24 for use in a topical treatment of a skin condition involving dry or inflamed skin, comprising an antimicrobially active nitroimidazole drug, a water miscible alkylene glycol, a hydroxyalkyl cellulose gelling agent and water, buffered to have a pH within the range of 4.5–6.5,and having a viscosity within the range of 10,000 cps to 200,000 cps.

26. A viscous hydrogel composition as claimed in claim 25, with a viscosity of 50,000 to 200,000 cps.

27. A composition as claimed in claim 25, consisting essentially of an antimicrobially active nitroimidazole drug, a water miscible alkylene glycol, a hydroxyalkyl cellulose gelling agent and water.

28. A composition as claimed in claim 25, wherein the hydroxyalkyl cellulose gelling agent is hydroxymethyl, hydroxyethyl or hydroxypropyl cellulose.

29. A composition as claimed in claim 28, wherein the hydroxyalkyl cellulose gelling agent is hydroxyethyl cellulose.

30. A composition as claimed in claim 25, wherein the antimicrobially active nitroimidazole drug is metronidazole or tinidazole.

31. A composition as claimed in claim 30, wherein the antimicrobially active nitroimidazole drug is metronidazole.

32. A composition as claimed in claim 25, further comprising a buffer system selected from the group consisting of acetic acid/acetate, hydrochloric acid/citrate, citric acid/citrate, citro-phosphate, phosphate and phosphate buffered saline.

33. A composition as claimed in claim 32, comprising citric acid and a citrate as buffering agents.

34. A composition as claimed in claim 25 having a pH within the range of 5–6.

35. A composition as claimed in claim 34 with a pH of about 5.5.

36. A composition as claimed in claim 25, wherein the hydroxyalkyl cellulose gelling agent is insoluble or substantially insoluble in the water miscible alkylene glycol.

37. A composition as claimed in claim 25, wherein the water miscible alkylene glycol is glycerol, dipropylene glycol, propylene glycol, butylene glycol, pentylene glycol or hexylene glycol.

38. A composition as claimed in claim 37, wherein the water miscible alkylene glycol is propylene glycol.

39. A method of treating a skin condition involving dry or inflamed skin, comprising topically applying a composition of claim 24 to skin affected by said condition.

40. The method as claimed in claim 39 wherein the skin condition is selected from the group consisting of rosocea, eczema and a condition involving an infection responsive to an antimicrobially active nitroimidazole drug.

41. The method as claimed in claim 40 wherein the antimicrobially active nitroimidazole drug is metronidazole.

42. A method of treating a skin condition involving dry or inflamed skin, comprising topically applying a composition of claim 25 to skin affected by said condition.

43. The method as claimed in claim 42 wherein the skin condition is selected from the group consisting of rosacea, eczema and a condition involving an infection responsive to an antimicrobially active nitroimidazole drug.

44. The method as claimed in claim 43 wherein the antimicrobially active nitroimidazole drug is metronidazole.

\* \* \* \* \*